United States Patent
Doering (10) Patent No.: US 11,801,485 B2
(45) Date of Patent: *Oct. 31, 2023

(54) METHOD AND APPARATUS FOR CONTROLLING A REACTOR

(71) Applicant: Andreas Doering, Unterhaching (DE)

(72) Inventor: Andreas Doering, Unterhaching (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/354,901

(22) Filed: Jun. 22, 2021

(65) Prior Publication Data

US 2022/0401901 A1 Dec. 22, 2022

(51) Int. Cl.
*B01J 3/00* (2006.01)
*B01J 3/03* (2006.01)
*C01B 3/48* (2006.01)
*C07C 1/12* (2006.01)

(52) U.S. Cl.
CPC .................. *B01J 3/002* (2013.01); *B01J 3/03* (2013.01); *C01B 3/48* (2013.01); *C07C 1/12* (2013.01); *C01B 2203/0233* (2013.01); *C01B 2203/0283* (2013.01); *C01B 2203/1241* (2013.01)

(58) Field of Classification Search
CPC .... B01J 3/002; B01J 3/03; C01B 3/48; C01B 2203/0233; C01B 2203/0283; C01B 2203/1241; C07C 1/12
See application file for complete search history.

(56) References Cited

U.S. PATENT DOCUMENTS

2007/0215520 A1* 9/2007 Edwin ...................... D01F 9/133
                                                                    208/46
2015/0377178 A1* 12/2015 Bussieres ................. F02F 1/14
                                                                    123/41.72

FOREIGN PATENT DOCUMENTS

EP          0088427      *  3/1983  ............... C07C 2/62

* cited by examiner

*Primary Examiner* — Jafar F Parsa
(74) *Attorney, Agent, or Firm* — Laurence A. Greenberg; Werner H. Stemer; Ralph E. Locher (57) ABSTRACT

The process and apparatus according to the invention allow the production of chemical compounds without the use of catalysts. For this purpose, the reactants necessary for the desired products are fed to compression reactors. In addition, the reaction conditions are controlled by means of an electronic control device. For this purpose, among other things, the compression reactors are combined with an electric motor, thereby influencing the residence time in the reactors. In addition, it is planned to raise the reactant pressures with the help of a compressor. In addition, the operating conditions are recorded with suitable sensors and/or analysers.

24 Claims, 6 Drawing Sheets

METHOD AND APPARATUS FOR CONTROLLING A REACTOR

BACKGROUND OF THE INVENTION

In the production of chemical products, the use of flow or fixed bed reactors is common because they are relatively inexpensive and easy to manufacture. So-called pulsed compression reactors represent another possible process control. This type of reactor is generally described e.g. in U.S. Pat. No. 8,691,079 B2, U.S. Pat. Nos. 2,814,551, 2,814,552 and in ""Pulsed Compression Technology: A Breakthrough in the Production of Hydrogen", M. Glouchenkov and A. Kronberg, WHEC 16/Jun. 13-16, 2006". The basic idea is that gaseous reactants respectively educts are fed into a reaction chamber via at least one inlet valve, this gas mixture is then compressed via a piston and thus heated. The desired reaction is initiated by the raised temperature, then the pressure and thus the temperature drop again due to the piston movement and the products thus produced then leave the reaction chamber via at least one outlet valve. This process is repeated periodically, comparable to an internal combustion engine. The difference, however, is that in internal combustion engines the main focus is on the energy generated and the exhaust gas is released into the atmosphere, whereas in pulsed compression reactors the goal is to obtain usable products. In this way, temperatures of well over a thousand Kelvin and pressures of several hundred bar can be represented for short periods of time without placing too high a load on the reactor components, since the subsequent expansion of the gas causes the reaction mixture to cool and thus reduces the component load. In order to utilise the energy dissipated during the expansion, at least two reaction chambers are usually mechanically coupled in such a way that the expansion of one reaction chamber leads to a compression in the second reaction chamber. This can be realised e.g. by a free piston arrangement (U.S. Pat. No. 8,691,079B2, "Pulsed Compression Technology: A Breakthrough in the Production of Hydrogen", M. Glouchenkov and A. Kronberg, WHEC 16/Jun. 13-16, 2006). A connection of two opposing, counter-rotating pistons, each closing off a reactor chamber, can also be realised (U.S. Pat. No. 2,814,551). The state of the art also includes reactors based on reciprocating piston engines that operate as reformers and are used to produce syngas (Lim, Emmanuel G. et al. "The Engine Reformer: Syngas Production in an Engine for Compact Gas-to-Liquids Synthesis." The Canadian Journal of Chemical Engineering 94.4 (2016): 623-635). However, pulsed compression reactors have not been widely used for the following reasons:

1. due to friction losses, the expansion work of one reaction chamber is often insufficient to provide enough energy to compress the other chamber by the piston. In U.S. Pat. No. 2,814,551 it is described that in such a case additional gas, mostly inert gas, is blown into the reactor chamber to increase the pressure there. In this way, the energy available for compression can be increased, but this requires additional valves and compressors.

2. the process is very difficult to control, since e.g. the frequency of the piston movements and thus the residence time depend on the energy released in the reaction and thus on the amount of reactant supplied.

3. the apparatus must be started pneumatically, which necessitates a large number of valves and a complicated piping.

4. relatively high temperatures and pressures must often be realised in order to achieve sufficiently high activation energies to start the reaction. This can be disadvantageous with regard to the selectivity of the reaction.

5. Since no direct control of the start of the reaction is possible, but it is started purely by pressure and temperature, this can already take place before the top dead centre of the piston, which has the consequence that it is on the one hand mechanically heavily loaded and on the other hand decelerated. The latter point can lead to not reaching top dead centre at all and the pulsating compression reactor coming to a standstill.

BRIEF SUMMARY OF THE INVENTION

Proceeding from the previously described state of the art, it is an object of the present invention, while avoiding the drawbacks of the known arrangements, to provide a method respectively process as well as an apparatus which enables superior control of pulsed compression reactors. For this purpose, the reactants necessary for the desired products are fed to compression reactors. In addition, the reaction conditions are controlled by means of an electronic control device. For this purpose, among other things, the compression reactors are combined with an electric motor, thereby influencing the residence time in the reactors. In addition, it is planned to raise the reactant pressures with the help of a compressor. In addition, the operating conditions are recorded with suitable sensors and/or analysers.

BRIEF DESCRIPTION OF THE DRAWINGS

This object, and other objects and advantages of the present invention, will appear more clearly from the following specification in conjunction with the accompanying schematic drawings.

DETAILED DESCRIPTION OF THE INVENTION

The invention disclosed in claims 1 to 20 is based on the topic of presenting a method or process as well as an apparatus which enables superior control of pulsed compression reactors. The method according to the invention solves these problems according to the generic term of claim 1, the apparatus according to the invention solves these problems according to the generic term of claim 19.

According to the invention, it is envisaged to influence the reaction conditions of a reciprocating compression reactor or a rotary piston reactor by changing the operating parameters of the compression reactors with the aid of an electronic control system which evaluates sensors and/or calculates mathematical models and controls actuators, in order to optimise the yield and/or selectivity of at least one desired product. For this purpose, actual values obtained via sensors and/or analysers are compared with setpoint values stored in the electronic control unit and operating parameters of the reactors are changed via suitable actuators in such a way that the actual values approach the setpoint values. Furthermore, according to the invention, it is provided that the maximum yield and/or selectivity of at least one product is used as the setpoint and an independent optimisation of the operating parameters of the reactors takes place in the electronic control unit. This is particularly useful if the quality or composition of the reactants respectively educts supplied fluctuates.

The continuous optimisation of the operating parameters means that the reactors continue to be operated in their optimum operating range, i.e. the electronic control unit continuously re-learns itself. This automated learning is state of the art in neural networks or artificial intelligence, so it will not be discussed further here. In contrast to the prior art, in which different reactors or catalysts must be used for different products, the process according to the invention and the associated apparatus offer the advantage that the operating parameters of the compression reactors, such as reaction temperature, residence time, reaction pressure, reactant or educt composition, valve opening and valve closing timing, can be changed over a wide range in such a way that a wide variety of products can be produced with the same apparatus.

In reciprocating compression reactors, at least two reactor chambers are designed in the form of cylinders and arranged in a row representing the so called in-line design. A two-row arrangement in the form of so-called banks is also possible, whereby the two banks are arranged tilted to each other forming a V-shape. In both cases, i.e. in-line or V-shaped, all pistons moving in the cylinders act on a common crankshaft via a connecting rod. In other words, the design is similar to a reciprocating piston engine.

A device, e.g. an electric machine, is coupled to this crankshaft, which can be used to change the speed of the shaft and thus the residence time in the reaction chambers: If the residence time is to be increased, the crankshaft is decelerated with the aid of the at least one device, if the residence time is to be reduced, the crankshaft is accelerated with the aid of the device, or the braking torque of the device is reduced. As electrical machines, e.g. commutators, such as direct current or single-phase alternating current motors, or rotating field machines, such as three-phase asynchronous machines, three-phase synchronous machines, single-phase asynchronous motors, single-phase synchronous motors, are used. Electric machines that can be used both as a motor and as a generator are preferable, as they can supply energy to the compression reactor on the one hand, but can also extract energy from it on the other, so that very flexible operation is possible. In addition, the energy to be dissipated during braking can be converted into electricity when the electric machine is used as a generator and fed into the power grid or made available to other electrical consumers. When using an electric machine as a motor, starting the apparatus is very simple, as the crankshaft is towed for this case. In addition, reactions can be realized in which the energy released by the reaction is not sufficient to ensure autarkic operation of the apparatus. This is particularly the case with endothermic reactions. In this case, the apparatus is driven by the electric machine. In addition to the above-described design as a reciprocating piston machine, a design as a rotary piston machine can also be implemented according to the invention. For this purpose, the rotor, analogous to the crankshaft, is also coupled to a device, e.g. an electric machine, via which the speed of the rotor of the rotary piston machine and thus the residence time in the reaction chambers can be changed. In addition, as already described above, the generation of electrical energy is thus possible. According to the invention, at least one of the resulting products has a calorific value of at least 12 MJ/kg, advantageously of at least 20 MJ/kg, extremely advantageously of at least 30 MJ/kg. The proportion of the at least one product with a calorific value of at least 12 MJ/kg in the material stream leaving the reactor is at least 5%, advantageously at least 10%, extremely advantageously at least 20%. The process is advantageous if the sum of the energy contents of the products is higher than the sum of the energy contents of the reactants respectively educts. Products include aliphatic hydrocarbons ($C_2H_2$, $CH_4$, etc.), aromatic hydrocarbons, alkaloids, amino acids, fats, heterocycles, $NH_3$, alcohols ($CH_3CH_2OH$, $CH_3OH$, etc.), HCHO, $C_2H_2$, $CH_3OH$, etc.).), HCHO, $C_2H_4$, ethers (dimethyl ether (DME), diethyl ether (DEE), polyoxymethylene dimethyl ether (POMDME) etc.), amines, amides, urea, $CS_2$, thiocyanates, carbamate, organic acids (e.g. acetic acid). For this purpose, one, advantageously at least two, of the following compounds or their derivatives are fed to the reactor chambers: $N_2$, $H_2$, CO, $CO_2$, aldehydes, in particular HCHO, alcohols, in particular $CH_3OH$ and ethanol, sulphur, methane, $NH_3$. If only methane is supplied, no oxygen is supplied at the same time. In the case of the other compounds, in the event that oxygen is added, always less oxygen is added than would be necessary for complete oxidation of the compound, according to the invention less than 80%, advantageously less than 40%, particularly advantageously less than 20% of the amount of oxygen which would be necessary for complete oxidation.

According to the invention $CH_4$ can be produced from CO or $CO_2$ and $H_2$ according to the following equations by feeding the reactants respectively educts to the reactor.

$$H_2 + CO_2 \rightarrow CO + H_2O$$

$$3H_2 + CO \rightarrow CH_4 + H_2O$$

To increase the yield, unused $H_2$ and $CO/CO_2$ are separated from the resulting product stream and fed back into the reactor. The same reactants respectively educts are also used for the production of methanol and ethanol, but less hydrogen is added per carbon atom.

$$CO + 2H_2 \rightarrow CH_3OH$$

$$CO_2 + 3H_2 \rightarrow CH_3OH + H_2O$$

$$2CO+4H_2 \rightarrow CH_3CH_2OH+H_2O$$

$$2CO_2+6H_2 \rightarrow CH_3CH_2OH+3H_2O$$

$N_2$ and $H_2$ are used to produce ammonia.

$$N_2+3H_2 \rightarrow 2NH_3$$

Methane and sulphur are fed to the reactors to form $CS_2$, $CS_2$ and $NH_3$ are fed for ammonium thiocyanate production, $CO_2$ and $NH_3$ are fed for ammonium carbamate production, ammonium carbamate is fed for urea production, methanol and carbon monoxide are fed for acetic acid production, methane is fed for ethyne production, ethyne and oxygen are fed for acetaldehyde production.

A further improvement of the process and method according to the invention, in particular with respect to the reactions described above, can be achieved if, in addition to the reactants respectively educts, at least one compound or substance for accelerating the desired reaction by lowering the activation energy, in particular a catalyst, is also fed to the reactor chambers. These are liquid, dissolved in a liquid or gaseous substances. In the example of ethanol production from ethane, this is phosphoric acid, which is subsequently separated from the ethanol formed and fed back into the process. Sulphuric acid can be used as a further catalyst. The formation of methanol can be improved by adding organo-zinc compounds, such as zinc methyl or zinc ethyl to the reactor chambers. The formation of methane can be improved by the addition of organonickel compounds, such as nickel tetracarbonyl, nickel-olefin complexes, such as bis-[cyclooctadiene-(1,5)]nickel(0), nickel-cyclopentadienyl complexes, such as nickelocene, nickel-allyl complexes, such as bis(π-allyl)nickel $[Ni(\eta^3-C_3H_5)_2]$, nickel-phosphine complexes or nickel-carbene complexes. In addition to the formation of methane, organonickel compounds can be used for the oligomerisation of alkenes and alkynes, for coupling reactions, such as allyl and acryl halides, and the carbonylation reactions for the addition of CO to alkenes and alkynes, such as the formation of acrylic acid from acetylene, water and carbon monoxide. Other possible compounds, or catalysts, that can be used in the process of the invention are organoferrous compounds, such as ferrocene $[Fe(C_5H_5)_2]$. Among other reactions, these accelerate the formation of $NH_3$ from $N_2$ and $H_2$. Organo-aluminium compounds, such as triethylaluminium, can be used for the formation of olefins, e.g. ethene is the starting material. All the catalysts or compounds described for accelerating the desired reaction have in common that at least their metallic components are preferably separated from the product stream downstream of the reactors. According to the invention, it is further provided that they are subsequently processed and returned to the reactor chambers. Processing is necessary if the compound changes during the reaction or, in the case of a catalyst, it's poisoned. This is particularly the case with complexes and organometallic compounds.

Like mentioned above all the compounds and catalytic active substances added to the reactor are preferably in there non solid state and/or dissolved in a liquid to circumvent abrasion problems.

In order to increase the yield, it is also provided according to the invention to remove a partial product stream downstream of the reactor chambers and to feed it back to the reactor chambers. The reaction conditions in the reactor chambers at the start of the reaction are at least 50 bar, advantageously at least 60 bar, extremely advantageously at least 70 bar. The reaction temperatures at the start of the reaction are between 200° C. and 500° C., advantageously between 250° C. and 450° C., extremely advantageously between 280° C. and 400° C.

The reactants respectively educts for the production of further products, such as HCHO, are CO and/or $CO_2$ and $H_2$, for $CH_3OH$ and $CH_3CH_2OH$, CO and/or $CO_2$ as well as $H_2$, for DME, $CH_3OH$, for POMDME, $CH_3OH$ and HCHO, for DEE, ethanol. In order to achieve sufficiently high yields in reactions whose yield is negatively influenced by the presence of oxygen, the oxygen concentration at the beginning of the reaction is at most 1%, advantageously at most 0.5%, extremely advantageously at most 500 ppm. This avoids or reduces oxidation of the products and a reduction in their calorific value. For safety reasons, it is advisable to feed the reactive or combustible reactants respectively educts, such as hydrogen, ethanol, $CH_4$ or methanol, directly upstream of the inlet to the reactor chamber, i.e. downstream of the non-combustible reactants, or directly into the reactor chamber via a valve that is independent of the inlet valve. In this case, the reactor inlets and outlets are advantageously closed. This direct feed is also suitable for liquid reactants.

The compression ratio of the piston reactors is at least 1:8, advantageously at least 1:15, extremely advantageously at least 1:20. The residence time of the reactants in the reactor chamber is at most 10 s, advantageously at most 1 s, extremely advantageously at most 0.1 s. The crankshaft is surrounded by a so-called crankcase and fastened to the reactor walls by screws. The seals used at the joints are static seals, which ensures a significantly better seal to the outside than the dynamic seals on the pistons. However, these dynamic seals of the piston at the liner of the reactor chamber are still a critical point, as reactants can enter the crankcase via them. In conjunction with the oxygen present in the environment, this can lead to the formation of explosive mixtures, such as oxyhydrogen gas, and consequently to an explosion or deflagration in the crankcase. If toxic reactants or products are used, such as formaldehyde, these can leach into the environment, which should also be prevented. According to the invention, this is prevented by flushing the crankcase with non-flammable and non-toxic or low-toxic reactants, such as $N_2$, CO and/or $CO_2$, which are then fed to the reactor chamber. A further improvement can be achieved if the crankcase or the reactants and products contained therein are sucked out so that a lower pressure is established than in the environment. The at least one flammable or toxic reactant and/or product is then also introduced directly upstream of the reactor chamber or, preferable, directly into the reactor chamber via a valve independent of the inlet valve, advantageously closing both the reactor inlets and outlets.

In order to additionally increase the pressures in the reactor chamber, it is useful to supply the reactants respectively educts to the reactor chamber already at increased pressure. In the simplest case, this can be done via compressors, but a turbocharger arrangement is energetically more sensible, especially for exothermic reactions: In this case enthalpy is extracted from the heated product flow via a turbine, which is arranged downstream of the reactor chambers, and transferred via a shaft to a compressor on the reactant respectively educt side. The pressure on the reactant/educt side respectively upstream of the reactor and thus ultimately the pressure inside the reactor chamber can be changed via suitable measures, such as discharge or bypass valves on the reactant/educt and/or product side, variable turbine and/or compressor geometries. The apparatus can be designed as a two-stroke, four-stroke or four+2*X-stroke apparatus. The following description refers to, but is not limited to, a reactor chamber and an exemplary design as a reciprocating piston compression reactor or apparatus with the crankshaft mounted below the pistons.

Two-Stroke Apparatus:
1. intake and compression (piston moves upward)
2. main reaction and push-out respectively expulsion (piston moves downwards)

For this construction, valves can, but do not have to be completely dispensed with, as the piston alternately closes or releases the inlet and outlet.

Four-Stroke Apparatus:
1. intake/suction (inlet open, outlet closed, piston moves down)
2. compression (inlet and outlet closed, piston moves upwards)
3. main reaction and expansion (piston moves downwards)
4. expulsion/push-out (outlet open, inlet closed, piston moves upwards)

This design requires inlet and outlet valves at the reactor compartments. These can be driven by at least one camshaft. From the engine sector, additional devices are known by which the opening and closing timing of these valves can be varied and which are also used here, such as piezo actuators, hydraulic valve trains, adjustable camshafts, etc. These measures can be used to influence the reaction conditions in the reactor chamber. For example, it is possible to open the exhaust valve after the third cycle respectively stroke even before the piston reaches bottom dead centre in order to lower the pressure and thus the temperature in the reactor chamber more quickly than it would be possible via piston movement alone. In this way, it is possible to freeze the reactions and avoid undesired side reactions. In addition, the inlet valve can be opened before the top dead centre of the piston is reached in the expulsion stroke, in particular before the bottom dead centre of the piston is reached, so that products flow back to the reactant side respectively inlet side. This causes a mixture of products and reactants/educts to be sucked in during the next suction stroke, which increases the yield of products. A similar effect is achieved if the outlet valve remains open during the suction cycle respectively stroke, so that products are sucked back into the reactor chamber.

Four-Stroke+2*X Apparatus:

This is a further development of the four-stroke apparatus. In order to increase the yield and/or selectivity and/or conversion rate, the outlet valve is not opened in the fourth cycle respectively stroke, but at least one more compression and reaction cycle respectively stroke is connected.
1. intake/suction (intake open, outlet closed, piston moves downwards)
2. compression 1 (inlet and outlet closed, piston moves upwards)
3. main reaction 1 and expansion 1 (piston moves downwards)
4. compression 2 (piston moves upwards)
5. main reaction 2 and expansion 2 (piston moves downwards)
... repeat the compression and main reaction cycle respectively stroke x times
6+2*x: expulsion/push-out (outlet open, inlet closed, piston moves upwards)

x is an element of the natural numbers, so that in total cycle respectively stroke numbers of 6, 8, 10 etc. result. It is often useful to add at least one reactant for the second main reaction. This can be done, for example, by opening the inlet valve or directly adding at least one further reactant via an additional feed device into the reactor chamber. On the one hand, it is possible to feed one of the reactants that has already been fed in the first main reaction, which on the one hand can increase the yield and/or the selectivity. However, it is also possible to feed at least one reactant that is different from the reactants in the first main reaction, whereby a different product than in first main reaction can be selectively produced. The addition can be done, for example, by opening the inlet valve and sucking it into the reactor chamber or directly adding at least one reactant via an additional feeding device into the reactor chamber. Irrespective of the number of cycles respectively strokes, the yield can be further increased by removing a partial product stream downstream of the reactor chamber and returning it to the reactor chamber, in particular on the inlet side, i.e. the reactant side. The amount of product returned in this way can be varied using suitable actuators, such as valves and/or blowers. This is particularly useful for equilibrium reactions and/or reactions with volume increase, as the equilibrium can thus be shifted to the product side. The product stream can be returned without further treatment, but it is advantageous to separate individual products and return only these.

Another way to increase the yield is to separate unconsumed reactants from the product stream and feed them back to the reactors. The reaction can also be influenced by the temperature of the reactants that are fed into the reactor chamber. For example, the yield of endothermic reactions or reactions with volume increase can be raised if the temperature of the reactants is increased before they enter the reaction chamber. This temperature increase can be achieved in an energy-efficient manner by thermally coupling the reactant stream to the product stream downstream of the reactor chambers and/or the cooling medium of the compression reactor. The cooling medium is necessary to prevent the apparatus from overheating. In exothermic reactions, such as methane production from CO or $CO_2$ and $H_2$, or ammonia production from $N_2$ and $H_2$, cooling of the reactants is also useful. Since, as described above, the start of the reaction often cannot be initiated in a defined manner solely via the pressures and temperatures prevailing in the reactor chambers and/or the temperatures would have to be raised so much that this would have a negative effect on the selectivity, according to the invention additional energy is supplied to the reactor chamber in addition to the compression energy in order to exceed the activation energy and thus start the reaction. This can be done via at least one of the following methods or devices: Electrical spark (especially via a spark plug), corona discharge, microwaves and laser pulse.

To further increase the input of energy into the reactor chamber, a small separate ignition reactor chamber can be used, which is connected to the bigger main reactor chamber via openings. In this chamber, a different gas composition is usually selected by the introduction of reactants than in the main reactor chamber. For example, an ignitable gas mixture containing oxygen can be provided in this chamber, while the main reactor chamber contains no oxygen or at least significantly less oxygen. The gas mixture contained in the ignition reactor chamber is now ignited, e.g. via a spark plug, and the resulting pressure wave and flame front travel through the openings into the main reactor chamber, where they start the main reaction. Another way of actively influencing the start time and the course of the reaction is to feed at least one reactant which is required for the reaction and/or a compound for lowering the activation energy, in particular a catalyst, directly into the reactor chamber at defined times. By this method, the reaction can be actively started and its progress as well as the selectivity and yield can be influenced. Advantageously, both the reactor inlets and the reactor outlets are closed for initiating the reaction. The activation energy for the conversion of the supplied reactants is therefore lowered thus the desired reaction is being initiated. Possible compounds and substances, in particular catalysts, for lowering the activation energy are described above. According to the invention, this addition takes place with closed inlet and outlet valves, in particular at the end of the compression stroke and/or at the beginning of the main reaction stroke, i.e. in the case of two-stroke apparatuses at the end of the first stroke and at the beginning of the second stroke, in the case of four-stroke units, at the end of the second and/or at the beginning of the third, in the case of four+2*X-stroke units, at the end of the second and/or second+2*x-th and/or at the beginning of the third and/or third+2*x-th, i.e. close to the top dead centre of the piston with the intake and exhaust valves closed. Since the reaction can only take place when the reactant, substance or catalyst necessary for the reaction is added, an uncontrolled reaction can be ruled out before it is added.

A further improvement can be achieved if at least one necessary reactant and/or the compound for lowering the activation energy, in particular a catalyst, are not only added completely at a defined time or position of the piston or crankshaft, but are distributed over several additions. According to the invention, the partial amounts and the timing of the individual reactant additions are controlled by an electronic control device. Furthermore, it is provided according to the invention that the total volume of the one reactant which is added in a distributed manner is less than or equal to the total volume of the other reactants which are not added in a distributed manner.

To increase the yield of the process, the product or gas composition is measured downstream of the reactor chamber and corresponding process parameters are adjusted via an electronic control unit. If, for example, the yield is too low, the following parameters, among others, can be adjusted: Crankshaft speed is lowered, reactant pressure is raised (for reactions with volume reduction), reactant pressure is lowered (for reactions with volume increase), amount of product returned to the reactant side is raised, the inlet valve is opened before the outlet valve opens, causing the products to flow to the reactant side, the energy supplied to the reactor is raised (e.g. raising the ignition voltage), the number of cycles respectively strokes is raised, especially above four.

If the selectivity is too low, at least the following is possible to increase it: The speed of the crankshaft is increased, the number of cycles respectively strokes until expulsion is lowered, the reactant pressure is lowered, the amount of product returned to the reactant side is lowered, in the intake cycle respectively stroke the inlet valve is closed before reaching bottom dead centre, in the expansion cycle respectively stroke the outlet and/or the inlet valve is opened before reaching bottom dead centre, the energy supplied to the reactor is pulsed and/or the individual energy is lowered (e.g. several laser pulses or ignition sparks).

This high degree of flexibility in reaction control clearly distinguishes the method and apparatus according to the invention from the prior art: in contrast to reaction systems and their corresponding apparatuses that are based on heterogeneous catalysis and that can only be used for a very specific reaction due to the different catalysts used in each case, the process parameters as well as the reactants and substances to influence the reaction can be varied over a very wide spectrum according to the invention, which distinguishes it from state of the art flow or pulsed reactors. This enables a wide variety of products to be produced by the same reactors from a wide variety of reactants just by varying the reactants, the reaction parameters and/or adding different substances to reduce the activation energy. The selection of the desired product and/or the control of the process is carried out, as already explained, with the aid of an electronic control device. This results in different modes of the process/method and the apparatus to produce different products.

For example, in a first mode methane can be produced from $H_2$ and $CO_2$ as reactants/educts, $$4H_2 + CO_2 \rightarrow CH_4 + 2H_2O$$

while in another mode methanol $$CO_2 + 3H_2 \rightarrow CH_3OH + H_2O$$

and in another mode dimethyl ether (DME)

$$2CH_3OH \rightarrow CH_3-O-CH_3 + H_2O$$

is produced. In this process, the individual reactor chambers can be operated in the same mode or in different modes or reaction conditions, as already described above. In the simplest case, the different modes differ with regard to the reaction conditions, but can also differ with regard to the reactants. According to the invention, the switching between different modes as well as the control and regulation is carried out with the aid of an electronic control unit. At least one of the following variables serves as control variables for the control: setpoint product composition, actual product composition, setpoint pressure curve in the reactor chamber, actual pressure curve in the reactor chamber, setpoint maximum pressure in the reactor chamber, actual maximum pressure in the reactor chamber, setpoint residence time in the reactor chamber, setpoint reactant pressure, setpoint reactant temperature, setpoint product temperature, setpoint reactant composition, setpoint pressure increase in the reactor chamber, actual pressure increase in the reactor chamber, actual rotational speed of the crankshaft or of the rotor, actual residence time in the reactor chamber, actual reactant pressure, actual reactant temperature, actual product temperature, actual reactant composition, setpoint of rotational speed of the crankshaft or of the rotor, actual residence time in the reactor chamber. At least one of the following variables, which can be adjusted via corresponding actuators, serve as control variables: educt quantities supplied, educt cooler output, educt heater output, educt pressure regulator, rotational speed of the electric machine, rotational speed of the crankshaft or rotor, energy supplied/discharged from the electric machine, inlet valve opening timing, outlet opening timing, inlet valve closing timing, outlet valve closing timing, recirculated product quantity, variation of compression ratio, variation of variable turbine geometry, variation of variable compressor geometry, product quantity bypassed the turbine, reactant/educt quantity discharged downstream of the compressor, position of a throttle valve on the reactant side, opening section of a back pressure valve on the product side, activation time of the additional energy supplied via a spark plug, a laser, microwaves or corona discharge, number of activations of the additional energy supplied via a spark plug, a laser, microwaves or corona discharge per working cycle respectively stroke, time and number of introduction of the reactant supplied directly into the reactor chamber with closed inlet and outlet valves. One possibility to further increase the yield and selectivity is to arrange at least one catalyst suitable for the respective reaction downstream of the reactor chambers. Since most of the reaction has already taken place in the compression reactors, it can be designed much smaller than usual. Using the example of methane production from $H_2$ and $CO_2$ and/or CO, a methanation catalyst is to be installed downstream of the reactor chambers. Nickel, rhutenium, aluminium, cobalt or cerium can be used as active components. In the case of $NH_3$ production from $H_2$ and $N_2$, however, iron-based catalysts are used. If a turbine is installed downstream of the reactors, the catalysts are advantageously installed upstream of this turbine, since at this position they operate at a higher pressure level.

Another advantage of the process, method and apparatus according to the invention is that the compression reactors can be used as compressors and conveyors for the resulting products. For this purpose, the outlets of the reactors are connected to at least one pressure vessel and/or a downstream process, in particular a process requiring a raised pressure. In the push-out cycle respectively stroke of the compression reactors, the resulting products are pushed out of the reactor and fed to the pressure vessel. I.e. the reactor works at the same time as a piston compressor according to the positive displacement principle. In the best case, an additional compressor or blower for conveying and compressing the at least one product can be dispensed with, or at least they can be designed to be significantly smaller. In exothermic reactions, the energy required for this purpose is provided from the chemical reaction, so that no conversion to another form of energy, such as electrical energy, is necessary. That's the reason, why the efficiency of the method and apparatus according to the invention is significantly higher than that of separately operating chemical flow or fixed-bed reactors and compressors. If the energy from the reaction is not sufficient, the conveying of the products or their compression can be carried out with the help of mechanical energy, which is transferred to the crankshaft via the electric machine.

DESCRIPTION OF SPECIFIC EMBODIMENTS

In the following, the apparatus according to the invention and the process respectively method are explained with reference to figures.

Figure 1:
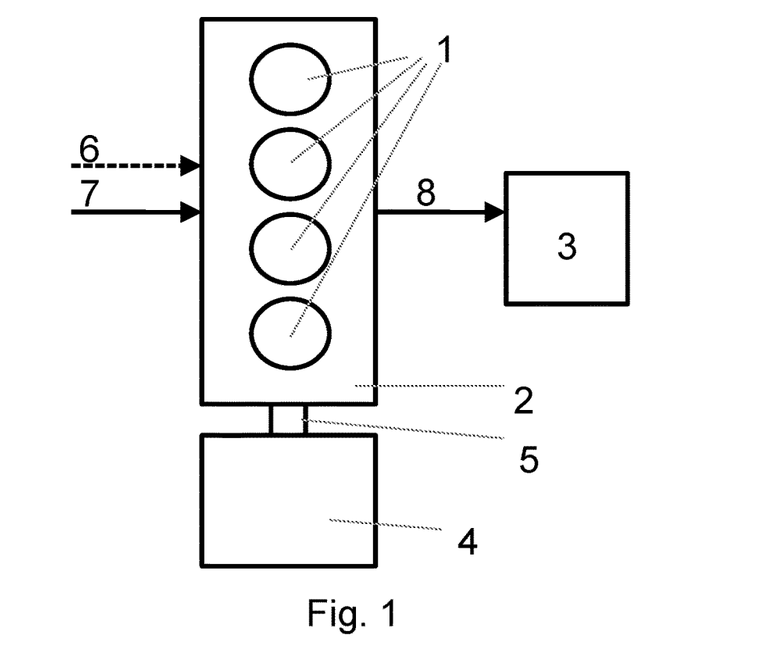
FIG. 1: Apparatus with the compression reactors chambers according to the invention

FIG. 1 shows the apparatus according to the invention. The individual reactor chambers (1) are arranged in series respectively in-line and accommodated in a common housing. Together they form a reciprocating compression piston machine (2). Via a shaft (5), the compression energy delivered by the reactors or to be supplied to them is transmitted to or from an electric machine (4). The reactants (6) and (7) are fed to the reactors, the products (8) are discharged from the reactor chambers (1) and collected in a container (3). To avoid overheating of the apparatus, it is cooled by a suitable cooling medium, such as water (not shown). In case of formation of several products and/or incomplete conversion of the reactants, a separation of the individual products or a separation of the reactants, e.g. via membrane processes, gas scrubbing, extraction, rectification, adsorption, condensation, is arranged downstream of the apparatus (not shown here). With the apparatus, methane can be produced as product (8) by adding $CO_2$ and/or CO as well as $H_2$ as educts, respectively reactants. The additionally produced water is separated from the methane as described above. Furthermore, the production of ammonia is possible by using nitrogen and hydrogen as reactants. Simultaneous production of $NH_3$ and $CH_4$ is also possible by feeding $CO_2$ and/or CO as well as $H_2$ and nitrogen to the reactors. The apparatus and method according to the invention are not limited to these compounds, but can be used in all reactions in which no solid, in particular no abrasive reaction products, are formed. These include, as already described above, in particular $NH_3$, HCHO, $CS_2$, thiocyanates (including ammonium thiocyanate), dimethyl ether (DME), diethyl ether (DEE), $CH_4$, POMDME, alcohols (methanol, ethanol), ammonium carbamate, urea, acetaldehyde, acetic acid.

Figure 2:
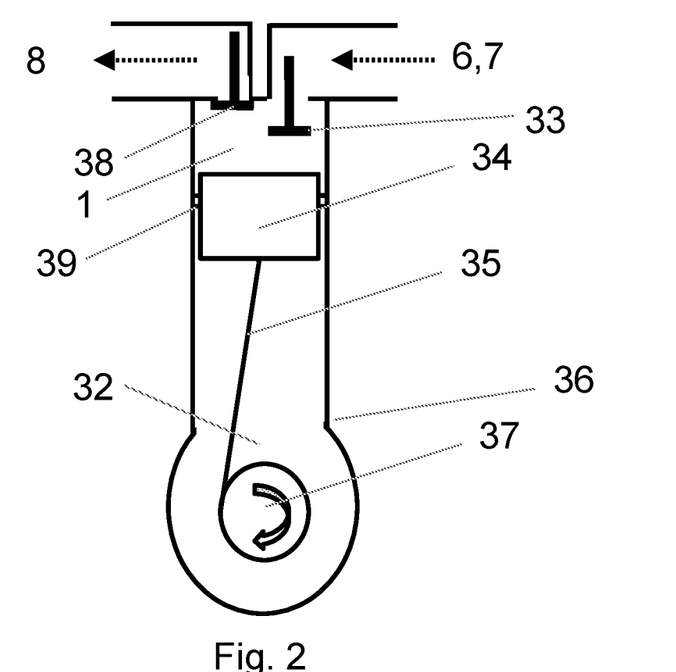
FIG. 2: Four stroke apparatus according to the invention

FIG. 2 shows a reactor according to the invention based on the four-stroke or the four+2*X-stroke principle: At least two reactants (6, 7) are fed into the reactor chamber (1) via at least one inlet valve (33). The reactants are sucked in and compressed via a piston (34), which is connected to the crankshaft (37) via a connecting rod (35) and which moves up and down in a cylinder, and the products (8) are then pushed out. The reactants can be fed to the reactor together via the inlet valve, as shown in FIG. 2. Particularly in the case of reactive and explosive substances, such as $H_2$, it is advisable for safety reasons to feed them directly into the reactor chamber, especially if the reactor inlets and outlets are closed, or at least to add them directly upstream of the inlet valve (not shown here). The compression results in an increase in temperature and pressure, which initiates the desired reaction. The start of the reaction can also be initiated, or precisely controlled or regulated, by adding additional energy, e.g. in the form of a spark plug, a laser pulse, a corona discharge or microwave radiation or required reactant addition (not shown here). To prevent educts respectively reactants and products from penetrating into the environment, the piston and the crankshaft are surrounded by a housing (32) that is sealed off from the environment by means of static seals (36). To prevent large quantities of reactants and products from entering the housing past the piston, the latter is sealed by means of dynamic seals (39) with respect to the cylinder in which it moves up and down. The at least one intake and/or exhaust valve can be controlled via camshafts, hydraulically or piezoelectrically. Especially the last two variants are to be preferred if a precise control of the reaction conditions and/or four+2*X-cycles respectively strokes are to be represented, since the valve opening timing can be freely chosen.

According to the method of the invention, the control and regulation is carried out with the aid of an electronic control device. The input variables for the control are at least one of the following variables whose setpoint and actual values: product composition, pressure curve in the reactor chamber, maximum pressure in the reactor chamber, pressure rise in the reactor chamber, speed of the crankshaft, residence time in the reactor chamber, reactant pressure, reactant temperature, product temperature, reactant composition, reactant quantity. At least one of the following variables serve as actuators or controlling variables: reactant quantity, reactant cooler rating, reactant heater rating, reactant pressure regulator, electric motor speed, crankshaft speed, energy supplied/dissipated from electric motor, valve opening timing (inlet valves, outlet valves), product quantity recycled, variation of compression ratio, variable turbine geometry, variable compressor geometry, amount of product bypassing the turbine, amount of reactant discharged after compressor, throttle valve on the reactant side, back pressure valve on the product side, activation timing and duration of the energy additionally supplied via a spark plug, a laser, microwaves or corona discharge, number of activations of the energy additionally supplied via a spark plug, a laser, microwaves or corona discharge per working cycle respectively stroke, timing and number of feeds of the reactant fed directly into the reactor chamber with closed inlet and outlet valves and/or of the at least one substance for lowering the activation energy, in particular of a catalyst. In particular, the pressure curve, the maximum pressure and the pressure increase gradient within the reactor chambers have proven to be important process variables. These variables or values can be determined with the aid of pressure sensors fluidically connected to the respective reactor chamber and corresponding evaluation in the electronic control unit. In addition to their influence on conversion and selectivity, these variables are also important in order to avoid mechanical overloading of the compression reactors. To ensure that no overloading occurs, their values are limited with the help of the electronic control unit. This is achieved in particular by reducing the quantities of reactant/educt supplied and/or lowering the quantity of reaction accelerating compounds/catalysts and/or lowering the reactant temperatures and/or reactant pressures and/or the compression ratio and/or increasing the quantity of product returned to the reactant side and/or shifting the additional activation energy supplied via e.g. spark plugs particularly to later points in time. An uncontrolled, very fast and early start of the reaction is particularly critical in this context, especially if it takes place well before top dead centre. These uncontrolled reactions can lead to detonations in the reactor chamber, which place a very high mechanical and thermal load on the components of the compression reactors. In addition to determining this state by means of the pressure sensors described above, which are connected to the respective reactor chamber, it is also possible to determine the uncontrolled, impact-like reactions with the aid of structure-borne sound sensors, in particular with the aid of piezoelectric longitudinal elements, and acceleration sensors which are arranged outside the reactor chambers on the apparatus according to the invention. Their signals are evaluated in an electronic control unit and compared with expected values. If an uncontrolled reaction is detected, the countermeasures already described above can be initiated via the electronic control unit.

In addition to preventing mechanical damage due to excessive reactor pressures or excessive pressure rise gradients, the pressure and/or structure-borne sound and/or acceleration sensors described above can also be used to detect a reaction that is too slow or the complete absence of a reaction. In these cases, the yield would drop considerably and a large amount of unreacted reactants/educts would reach the product side. In this case, the electronic control unit would increase the supplied reactant quantities and/or the quantity of reaction-accelerating compounds/catalysts and/or the reactant temperatures and/or reactant pressures and/or the compression ratio and/or reduce the quantity of product returned to the reactant/educt side and/or the additional activation energy supplied via e.g. spark plugs is shifted to earlier points in time and/or the addition of reactant and/or compounds to reduce the activation energy introduced directly into the reactor chamber with closed inlet and outlet valves is shifted to earlier points in time and/or the number of additionally supplied activation events, such as e.g. electric sparks, and/or the number of reactant additions made directly into the reactor chamber and/or the amount of additionally supplied activation energy is increased.

The problem of the reaction being too slow or completely absent occurs in particular at the start of the compression reactors, since their components in contact with the reactant and in particular the reactor chambers are still cold at this time. This can lead to the setpoint reaction temperatures not being reached. In order to avoid this, it is provided in accordance with the invention that, when starting the compression reactors, they are operated in a dragged mode before all reactants are fed to the reactor chambers. As described above, this is achieved in the simplest case with the aid of an electric motor coupled to the crankshaft of the reciprocating compression reactors. Furthermore, according to the invention, it is provided to preheat the coolant and/or the lubricant of the reciprocating compression reactors before a start. Furthermore, until the operating temperature or the desired product composition is reached, a valve arranged downstream of the reactor chambers and downstream of the line for returning the products to the educt side is closed or at least reduced and a line for returning the products to the inlet, i.e. inlet/educt side, is opened. This results in a recirculation of the gases to the inlet/educt side. Due to the friction and the resulting frictional heat, the temperature in the reactor chambers increases, and this effect is intensified by the recirculation of the heated fluids to the inlet side. Independently of or in addition to this, not all the reactants/educts required for the desired reaction are added during this start up procedure, but rather preferably inert substances, in particular reactants such as $N_2$ or $CO_2$. This is particularly useful when explosive reactants are added in the actual reaction, as this flushes the reactor chambers and removes any oxygen that may have penetrated during the standstill. It is particularly advantageous to add gases with a positive Joule-Thomson coefficient to the reactor chambers before the operating temperature is reached, since the temperature of these gases increases due to compression in the reactor chambers, which warms up the reactor chambers. The addition of gases with a negative Joule-Thomson coefficient, such as hydrogen, is dispensed during this operating phase. In addition, preheating of the reactants is possible. If the electronic control unit detects a sufficiently high temperature for the reaction, it switches from the warm-up mode to the actual standard mode to produce the desired products. I.e. all reactants are now added, the valve downstream of the reactor is opened and the amount of product or reactants returned to the reactant side is adjusted to the desired product composition (see also FIG. 4).

Figures 3A, 3B, 3C:
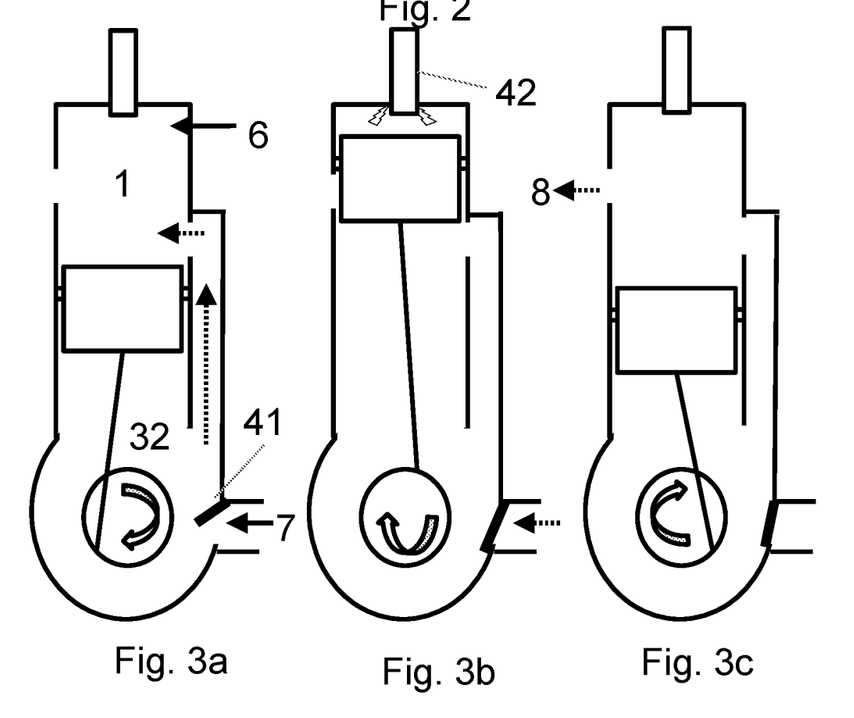
FIG. 3a: Two stroke apparatus according to the invention during the suction stroke
FIG. 3b: Two stroke apparatus according to the invention during the reaction phase
FIG. 3c: Two stroke apparatus according to the invention during the ejection stroke

The design as a two-stroke apparatus is shown in FIGS. 3a, b, c, but is not limited to this: according to the invention, in the first cycle respectively stroke (FIG. 3a), particularly the non-corrosive, non-flammable or non-explosive reactant (7) is fed into the housing (32) via a valve or flap. This flows past the piston into the reactor chamber (1). The at least second reactant (6) is added to the reactor chamber (1) or directly in front of it (not shown here). The upward movement of the piston compresses the reactants (FIG. 3b) and the reaction is initiated. This can be improved, or precisely controlled or regulated, by using a device (42) for feeding compounds to reduce the activation energy and/or a further reactant and/or supplying additional energy, such as a spark plug, a laser pulse, a corona discharge or microwave radiation. In the subsequent ejection cycle respectively stroke (FIG. 3c), the products (8) are discharged from the reactor. The supply of energy in addition to the compression energy and the separate supply of reactants or compounds for lowering the activation energy into the reaction chamber is not limited to the two-stroke apparatus, but can also be used in four- and four+2*X-stroke apparatuses.

Figure 4:
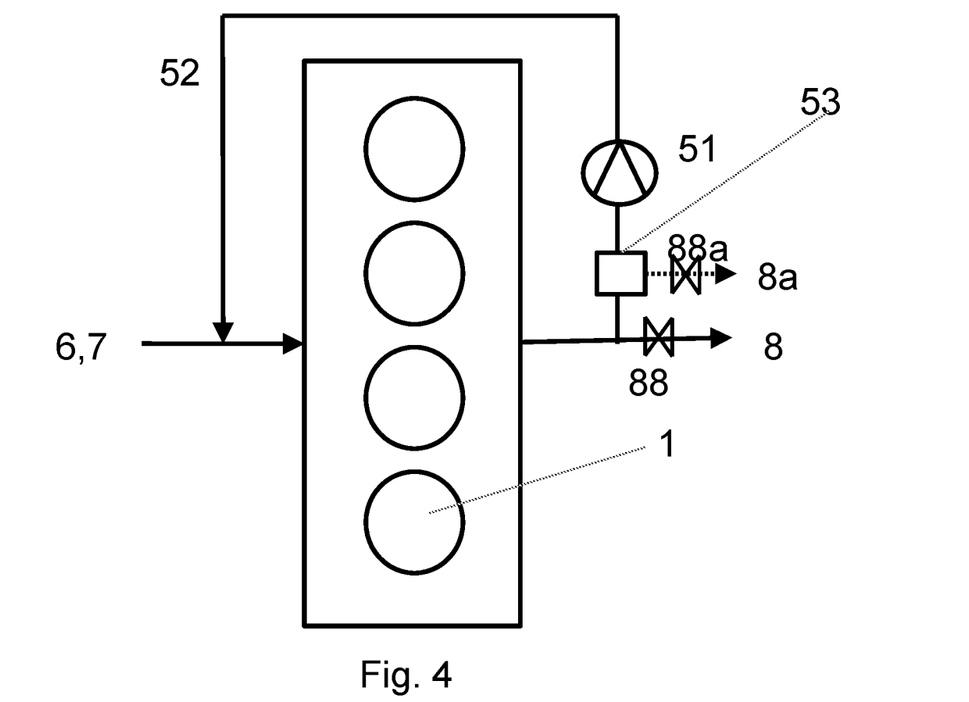
FIG. 4: Apparatus according to the invention with a partial recirculation of products

FIG. 4 shows a modification of the arrangement chosen in FIG. 1 to increase the yield and/or selectivity. Here, a product stream is extracted downstream of the reactors and this partial product stream (52) is added to the reactors (1) together with the reactants/educts (6,7). To increase or control this stream (52) a suitable device (51), such as a compressor or a blower, can be added. A control of this recirculated product flow with suitable control elements, such as valves or flaps, can also be implemented (not shown). In order to further increase the yield or selectivity, it may be useful to selectively separate products (8a) from this stream via a separator device (53). In particular, if the product stream (8) still contains high amounts of reactants or undesired intermediate products or end products. For example, in the production of methane using CO and/or $CO_2$ as well as $H_2$, this is water that is discharged from the circulation. In addition, $CH_4$ can be discharged so that only unused reactants and unwanted by-products are redirected.

When the compression reactors are started, it is provided in accordance with the invention that the valve (88) and optionally the valve (88a) are closed or at least the flow through them is throttled so that the amount of recycled partial product stream (52) is raised to warm up the compression reactors as described above. For a detailed description of the start-up procedure, please refer to the description of FIG. 2.

Figure 5:
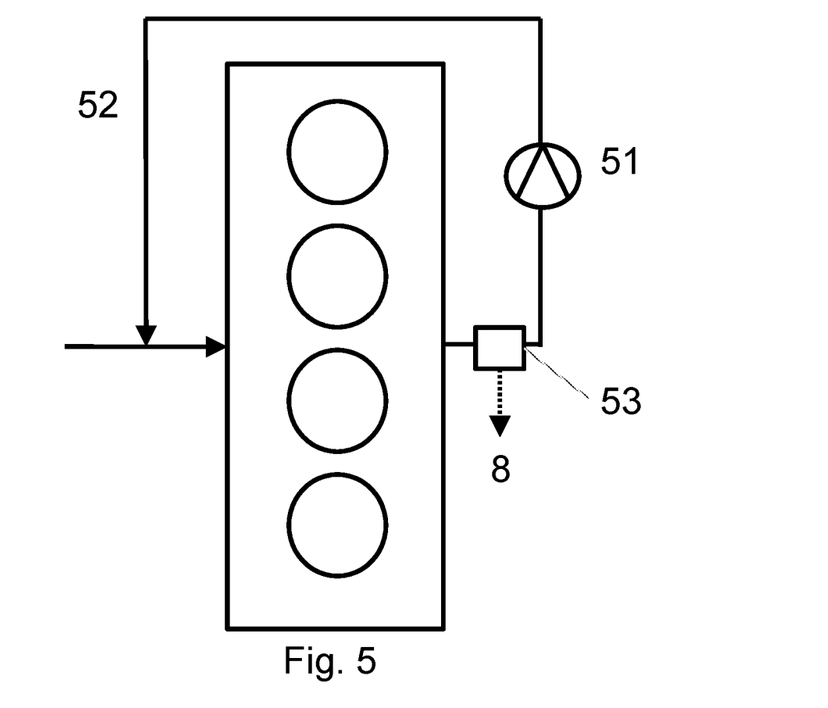
FIG. 5: Apparatus according to the invention with a partial recirculation of products
Figure 6:
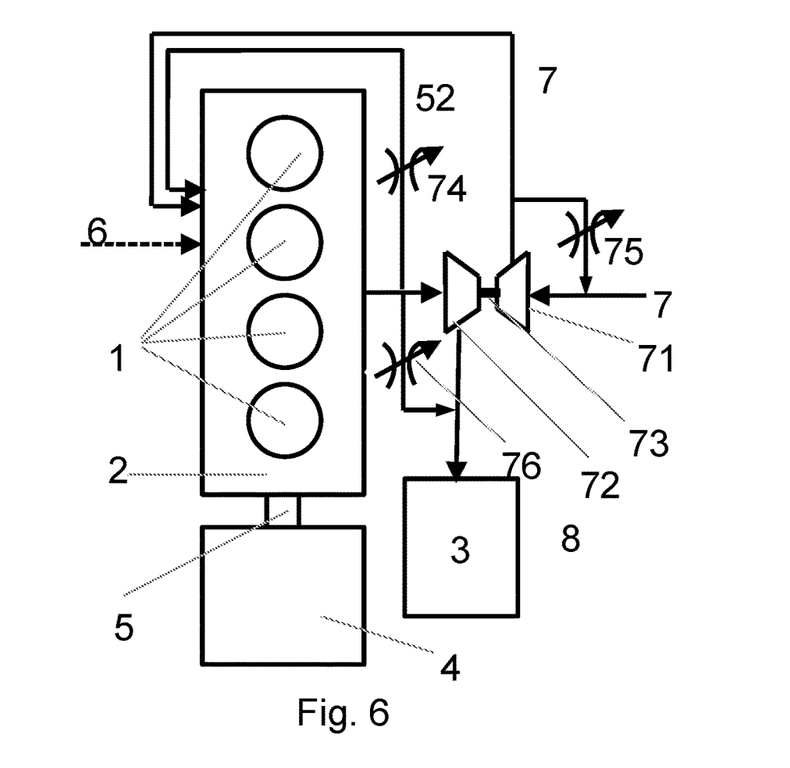
FIG. 6: Embodiment for raising the reactant pressure via a compressor

A similar set-up is shown in FIG. 5, but here the separator (53) is arranged in the main product stream, so that the separation of the product is implemented for the entire product stream. FIG. 6 shows an embodiment for increasing the educt respectively reactant pressure via a compressor (71). The compressed educt respectively reactant (7) is then fed to the reactors. The at least second reactant (6) can be added to this reactant (7) upstream of the compressor (not shown), or added directly upstream of the reactors or directly into the reactors via a valve independent of the inlet valve. The compressor (71) is connected via a shaft (73) to a turbine (72) via which the product flow (8) is expanded from a high to a lower pressure. The energy released in this process is thus largely used again for compressing the reactants, which increases the efficiency of the process. The reactant pressure and thus the pressure in the reactor chambers can be varied by suitable devices, such as blowing off the reactant from the high-pressure to the low-pressure side of the compressor via a suitable control element (75) (compressor bypass), blowing off the product from the high-pressure to the low-pressure side of the turbine via a suitable control element (76) (turbine bypass), variable turbine geometry and/or a variable compressor geometry. In order to further increase the pressure, the compressor can also be driven electrically and/or a further compressor can be arranged within the reactant/educt flow. It is also advantageous in this design if the system is designed in such a way that the pressure on the educt respectively reactant side is lower than on the product side, as this allows product, that is returned to the educt side respectively inlet side (52) to flow to the educt side without a conveying device such as compressors, blowers or pumps. The quantity can be varied or regulated via a variable throttle device (74) and an electronic control unit. According to the invention, it is provided that at least the temperature of a reactant respectively educt or of the product returned to the reactor is controlled or regulated by means of an electronic control unit and coolers or heaters (not shown).

Figure 7:
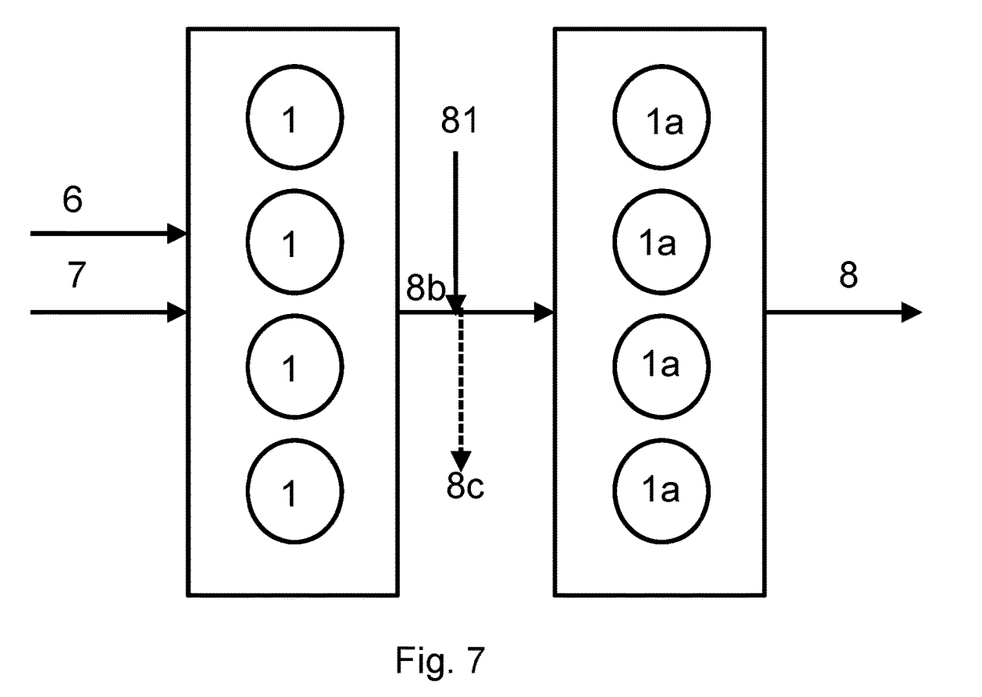
FIG. 7: Series arrangement of reactor chambers in respect to flow
Figure 8:
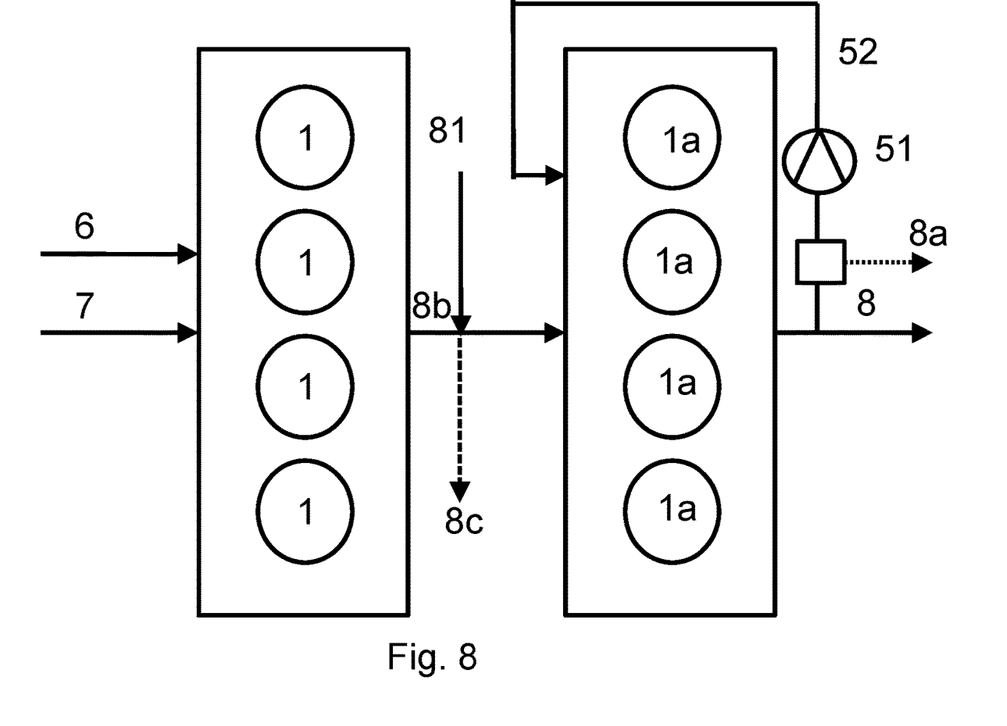
FIG. 8: Series arrangement of reactor chambers in respect to flow and partial recirculation of products

FIGS. 7 and 8 show a serial setup of several reactors (1) and (1a) in respect to the flow. The reactors (1) and (1a) can differ in their geometry, such as piston geometry, diameter and/or stroke, or in their operating parameters, such as temperature, pressure and/or additional energy supplied. This makes it possible to further process an intermediate product (8b) leaving the first reactors (1) with modified reaction conditions, resulting in the final product (8). Between the two reactors, another reactant (81) can be fed and/or an intermediate product (8c) can be discharged.

For example, methanol can be produced from $CO_2$ and $H_2$ in the first reactors (1), $$CO_2 + 3H_2 \rightarrow CH_3OH + H_2O$$

while in the second reactors (1a) dimethyl ether (DME) can be formed from this methanol (8b) by splitting off $H_2O$.

$$2CH_3OH \rightarrow CH_3-O-CH_3 + H_2O$$

Between the two reactors, an intermediate product, in this case $H_2O$, is removed from the product stream the first reactor respectively reaction (8c). This serves to shift the equilibrium to the side of DME. This can be further improved if the water formed in the second reactor is removed from the product stream (8a) and this water-free product stream (52) is returned to the reactor chambers (1a) (FIG. 8).

Another example of this process is the production of hydrogen from methane. In a first reactor chamber, steam reforming takes place.

$$CH_4 + H_2O \rightarrow CO + 3H_2$$

The resulting $CO/H_2$ mixture is then fed to the second reactor with the addition of water (81), in which further hydrogen is produced with the aid of the water gas shift reaction.

$$CO + H_2O \leftrightarrow CO_2 + H_2$$

The water gas shift reaction can be improved by removing the $CO_2$ formed in the second reactor from the product stream and feeding this $CO_2$-free product stream (52) back to the reactor compartments (1a) and/or discharging hydrogen (8c) between the reactors (1) and (1a) (FIG. 8).

Figure 9:
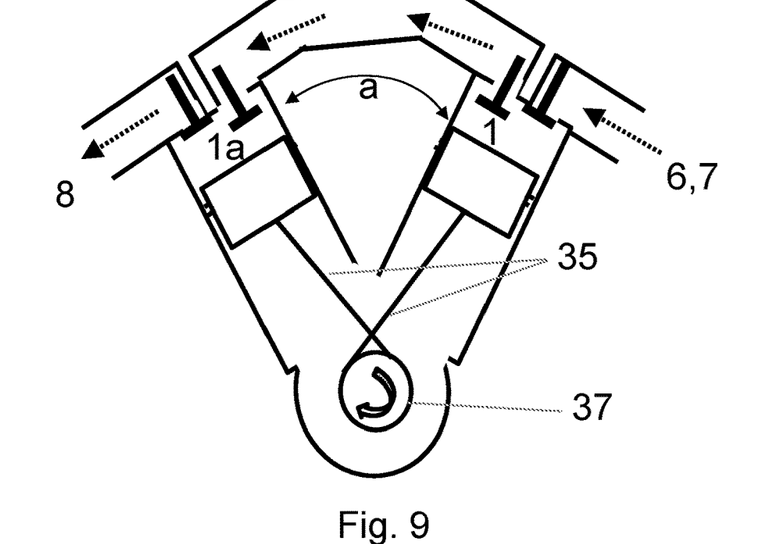
FIG. 9: Series arrangement of reactor chambers in the form a V-shape apparatus

The two reactor rows can be designed as separate independent units, i.e. separate piston machines, in the event that different residence times are to be realised in the two reactor rows. However, according to the invention it is also possible to arrange both rows of the reactors in such a way that their pistons act on a common crankshaft (37) via the connecting rods (35). This is particularly useful if the residence times in the two reactor rows are to be identical. To ensure this, the two rows are arranged in a V-shape relative to each other, the angle of the two legs being marked as "a" in FIG. 9.

Figure 10:
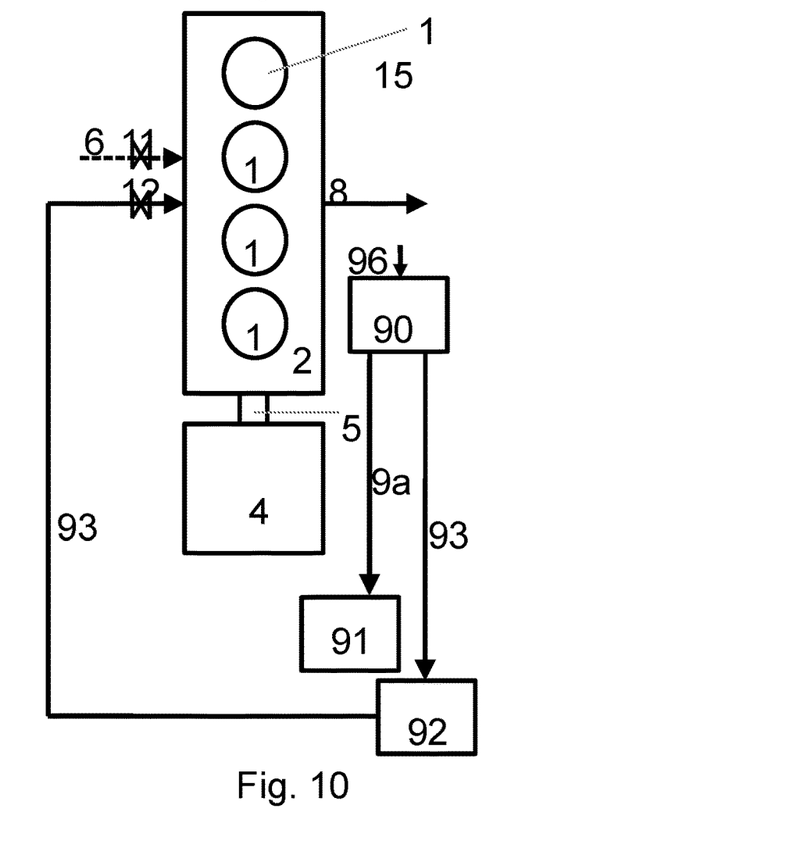
FIG. 10: General overview of the process respectively method

FIG. 10 shows a variant and a method of the apparatus shown in FIG. 2. In addition to the components already described in FIG. 2, a device (90) for splitting water (96) into hydrogen (93) and oxygen (9a) using electrical energy is also shown. This splitting of the water is illustrated with an electrolyser, whereby a high-temperature electrolyser can be used to improve the yields. To increase the efficiency, this can be thermally coupled to the product flow (8) and/or the cooling of the reciprocating machine (2) (not shown). The water (96) required for this electrolyser can be supplied externally. It is also possible to use water formed as a product in the reactor chambers. In the event that the reactors drive an electric machine operating as a generator, the electrical energy thus generated can be supplied to the electrolyser to improve the overall efficiency.

The process according to the invention is described below using the example of a process for $CH_4$ production. The hydrogen (93) leaving the electrolyser is fed together with CO and/or $CO_2$ (6) to the reactor chambers (1), whereby $CH_4$ and $H_2O$ are formed and leave the reactors (8). The water is then separated from the $CH_4$ (not shown here) and at least the $CH_4$ formed is collected. The oxygen (9a) formed by the electrolysis can be collected in a container (91) and then fed to other processes (not shown). The CO or $CO_2$ required for the reaction is obtained by burning carbon, especially compounds containing hydrocarbons.

Ammonia can be produced in the same way as methane, but instead of carbon monoxide or carbon dioxide, nitrogen (6) is fed to the reaction spaces together with hydrogen (93).

A parallel formation of methane and ammonia is also possible, if both nitrogen and CO and/or $CO_2$ as well as hydrogen are fed to the reactor chambers. Downstream of the reactor chambers, ammonia is separated via absorption, adsorption or membrane processes. This parallel production of ammonia and methane illustrates the major difference between the flow or fixed bed reactors equipped with solid catalysts and the process according to the invention: Unlike the flow and fixed-bed reactors, in which the two substances have to be produced on two different catalysts with separate reactant feeds and thus in two separate plants or steps, this is achieved according to the method according to the invention without solid catalysts for heterogeneous catalysis and by the use of just a single device. This significantly reduces both installation space and costs. In addition, no complex gas separation on the reactant side is necessary to separate $N_2$ from CO and $CO_2$, which is otherwise common.

In all three cases, the oxygen content in the reactor chambers must be minimised at the beginning of the reaction in order to achieve high selectivities for the desired products methane or ammonia. The hydrogen (93) produced in the electrolysis can be temporarily stored in a container (92).

Figure 11:
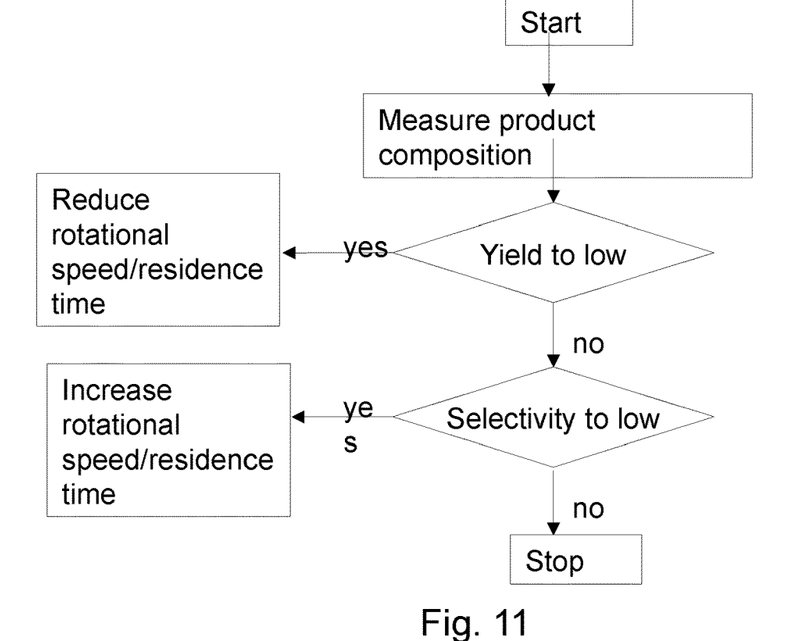
FIG. 11: Flowchart of the electronic control device program to optimize yield and selectivity

FIG. 11 shows the control of the process according to the invention with the aid of an electronic control unit using the example of the control of the crankshaft rotational speed and thus the residence time. In general, this control unit evaluates corresponding sensors for determining the reactant and product states, such as temperature, pressure and flow sensors as well as structure-borne sound, acceleration or speed sensors of the electric motor or the crankshaft, in order to represent a closed control loop. In addition, the pressure curve and/or the rate of pressure increase and/or the maximum pressure within the reaction chambers can be recorded by the control unit with the aid of pressure sensors. According to the invention, it is further intended to determine the product composition also with corresponding sensors, such as $NH_3$, $CO_2$, CO, $CH_4$ sensors and/or with the aid of analysers, such as gas chromatographs, IR, UV, FID analysers, FTIR and/or mass spectrometers. If the yield determined in this way is too low, the speed is lowered to increase the residence time. If, on the other hand, the selectivity is too low, the speed is increased and thus the residence time lowered. As described above, other process parameters such as recycled product amount, reactant pressures, reactant temperatures, product temperatures, product pressures, variable compression ratios, timing of additionally supplied activation energy, amount of additionally supplied activation energy, number of additionally supplied activation energy per cycle respectively stroke, reactant amounts, valve timing (for inlet and/or outlet valves), timing of reactant supplied directly into the reactor chamber, number of cycles respectively strokes, crankshaft speed, speed of the e-motor, temperature of the recycled product, etc. (not shown here), are also suitable for controlling the process (not shown here), in order to influence the reaction to the desired extent with the aid of the electronic control unit and suitable actuators.

Figure 12:
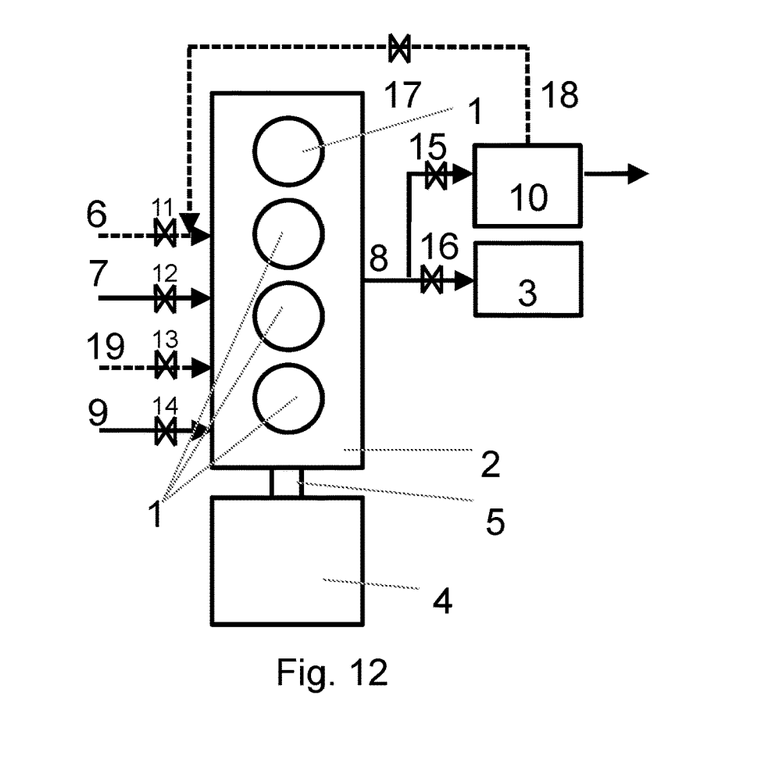
FIG. 12: Compression reactor according to the invention, which can be operated in at least two different modes to produce different products

FIG. 12 shows a apparatus according to the invention, which can be operated in at least two different modes for the production of different products, as well as the associated process. The individual reactor chambers (1) are arranged in series and housed by a common casing. Together they form a reciprocating engine (2). Via a shaft (5), the compression energy delivered by the reactors or to be supplied to them is transmitted to or from an electric motor (4). In a first mode, the reactants (9) and (19) are fed to it via the open valves (13) and (14) and products formed directed towards a container (10) via the valve (15) and/or directed towards another process. The valves (11), (12), (17), (16) are closed in this mode. In the second mode, the valves (13), (14) and (15) are closed and the valves (11), (12) and (16) are opened. As a result, the reactants (6) and (7) are fed to the reactors and the products (8) are discharged from the reactors (1) and collected in a second container (3). To avoid overheating of the apparatus, it is cooled by a suitable cooling medium, such as water. If several products are formed, a separation of the individual products is arranged downstream of the apparatus, e.g. via membrane processes, gas scrubbing, extraction, rectification, adsorption, condensation (not shown here). This becomes relevant, for example, when gases are fed in as educts that result from an oxidation reaction with air, such as those produced during the combustion of hydrocarbons in mode one. In this case, CO and $CO_2$ are formed on the one hand, but in addition large amounts of $N_2$ are contained, which do not participate in the combustion. If this mixture is fed into the reaction chamber together with $H_2$, hydrocarbons are formed, such as methane, but also water and $NH_3$. This $NH_3$ can be easily absorbed with the help of water, which is led in a column in countercurrent or co-current flow, at temperatures below 30°, preferably below 20° C., extremely preferably below 15° C. The water is then discharged and heated. This water is then discharged and heated to expel the $NH_3$ again, thus "regenerating" the water so that it can absorb $NH_3$ again. It is then cooled and returned to the product stream to absorb more $NH_3$. Since the water produced in the reaction is also separated from the hydrocarbons in this way, it is discharged, as otherwise the amount of water carried in the circuit would increase. The amount of heat required for the desorption of ammonia can be applied by thermally coupling the desorption to the product flow upstream of the scrubber and/or to the cooling medium of the reactor. FIG. 12 also shows another possible embodiment according to the invention: In the first mode, at least parts of the product stream are stored in a container (10). The remaining product components, on the other hand, are discharged into the environment or another container (not shown). Since the separation of gases and fluids is state of the art, reference is hereby made to these methods. In mode two, the valve (17) is opened and thus the product from mode one is fed to the reactor as reactant in mode two.

The control of the corresponding valves and the regulation of the entire process shown is carried out by an electronic control unit (not shown).

In most examples $NH_3$, $H_2$ or $CH_4$ were described above as products, but the method, process and the apparatus are not limited to these products, but can used for all reactions with gaseous reactants respectively educts or liquid reactants respectively educts which evaporate inside the reaction chambers.

The invention claimed is:

1. A method for optimizing at least one of a yield or selectivity of at least one product, the method comprising:
producing the product by using at least one pulsed compression reactor or rotary piston reactor or at least two pulsed reciprocating piston compression reactors mechanically coupled by a shaft;
connecting a rotary piston or the shaft of the reciprocating piston compression reactors to an electric machine;

using an electronic control device utilizing at least one of sensors or mathematical models to determine actual values of at least one of the compression reactor or products or reactants;

comparing the actual values with setpoint values stored in the electronic control device;

using the electronic control device to adjust the actual values by changing at least one or at least two or at least three operating parameters of the at least one compression reactor to meet the setpoint values; and providing at least one resulting product with a calorific value of at least 12 MJ/kg.

2. The method according to claim 1, which further comprises providing the at least one resulting product with a calorific value of at least 20 MJ/kg.

3. The method according to claim 1, which further comprises providing the at least one resulting product with a calorific value of at least 30 MJ/kg.

4. The method according to claim 1, which further comprises feeding at least one of at least one reactant or substance or compound or catalyst into a reactor chamber to at least one of initiate or accelerate a reaction or lower an activation energy, and adding the substance as gas or liquid or dissolving the substance in a liquid.

5. The method according to claim 1, which further comprises feeding at least one or at least two following compounds or derivatives of the following compounds to reactor chambers:

$N_2$, $H_2$, CO, $CO_2$, HCHO, $CH_3OH$, ethanol, or methanol.

6. The method according to claim 1, which further comprises raising a reactant pressure by using a compressor connected by a shaft to a turbine driven by a product stream.

7. The method according to claim 1, which further comprises operating reactor chambers at least at two different modes to produce different products.

8. The method according to claim 1, which further comprises downstream of a reaction chamber, extracting at least one of a reactant or a partial product stream or a product from a total product stream and feeding the reactant or partial product stream or product back to the reaction chamber.

9. The method according to claim 1, which further comprises changing at least one or at least two or at least three following values by using at least one electronic control device:

valve opening timing of at least one inlet valve,
valve opening timing of at least one outlet valve,
valve closing timing of the at least one inlet valve,
valve closing timing of the at least one outlet valve,
time of a reactant added directly into a reactor chamber,
rotational shaft speed,
reactant pressure of at least one reactant,
reactant temperature of at least one reactant,
reactant composition,
recycled product quantity,
temperature of recycled products,
variation of a number of cycles or strokes,
compression ratio,
time of additionally supplied activation energies independently of compression energy,
energy quantity of an additionally supplied activation energy,
number of cycles or strokes,
number of additionally supplied activation energies per cycle or stroke.

10. The method according to claim 1, which further comprises forming at least one following compound:

$NH_3$,
alkenes,
alkanes,
alcohols,
ethers,
esters,
$CH_4$,
$CH_3CH_2OH$,
$CH_3OH$,
C2H4,
HCHO,
dimethyl ether,
diethyl ether,
polyoxymethylenedimethyl ether.

11. The method according to claim 1, which further comprises operating a reciprocating or rotary piston engine as a two-stroke or four-stroke or four+2*X-stroke apparatus, where x is an element of natural numbers.

12. The method according to claim 1, which further comprises:

providing a separate ignition reactor chamber connected to a bigger main reactor chamber through openings;
igniting a gas mixture contained in the ignition reactor chamber; and
propagating a resulting pressure wave and flame front through the openings into the main reactor chamber to initiate a start of a reaction in the main reactor chamber.

13. The method according to claim 1, which further comprises:

feeding at least one substance or compound or catalyst into a reactor chamber to initiate or at least one of accelerate a reaction or lower an activation energy;
adding the at least one substance or compound or catalyst as a gas or a liquid or dissolving the at least one substance or compound or catalyst in a liquid; and
the at least one substance or compound or catalyst containing at least one following chemical compound:
phosphoric acid, sulphuric acid, organa-zinc compounds or zinc methyl or zinc ethyl organonickel compounds or nickel tetracarbonyl, nickel-olefin complexes or bis-[cyclooctadiene-]nickel, nickel-cyclopentadienyl complexes or nickelocene, nickel-allyl complexes or bis($\pi$-allyl)nickel [Ni($\eta^3$-$C_3H_5$)$_2$], nickel-phosphine complexes or nickel-carbene complexes, organoferrous compounds or ferrocene [Fe($C_5H_5$)$_2$], organoaluminium compounds or triethylaluminium.

14. The method according to claim 1, which further comprises placing at least two reaction chambers one behind another in terms of flow, and at least one of supplying at least one reactant or extracting at least one product.

15. The method according to claim 1, which further comprises placing at least two reaction chambers one behind another in terms of flow, and using different operating parameters for the at least two reaction chambers.

16. The method according to claim 1, which further comprises providing at least one device downstream of reaction chambers for separating individual substances from a product gas stream according to processes using a membrane, a gas scrubber, an extraction, a rectification, an adsorption, an absorption or a condensation.

17. The method according to claim 1, which further comprises placing at least one catalyst downstream of reaction chambers to increase yield.

18. The method according to claim 1, which further comprises, prior to a start of reactions in reactor chambers, setting temperatures to between 200° C. and 500° C., or between 250° C. and 450° C., or between 280° C. and 400° C.

19. The method according to claim 1, which further comprises setting a pressure in reactor chambers to at least 50 bar, or at least 60 bar, or at least 70 bar.

20. The method according to claim 1, which further comprises setting a proportion of the at least one product with a calorific value of at least 12 MJ/kg in the product stream leaving the reactor to at least 5%, or at least 10%, or at least 20%, of a whole product stream.

21. An apparatus for optimizing at least one of a yield or selectivity of at least one product, the apparatus comprising:
   at least one pulsed compression reactor or rotary piston reactor or at least two pulsed reciprocating piston compression reactors for producing the at least one product;
   a shaft mechanically coupling said at least one pulsed compression reactor or rotary piston reactor or at least two pulsed reciprocating piston compression reactors;
   an electric machine;
   said reciprocating piston compression reactors having a rotary piston or a shaft connected to said electric machine;
   an electronic control device and at least one of sensors or mathematical models determining actual values of at least one of said compression reactor or the at least one product or reactants, said electronic control device comparing the actual values with setpoint values stored in said electronic control device;
   said electronic control device adjusting the actual values by changing at least one, at least two or at least three operating parameters of said at least one compression reactor to meet the setpoint values; and
   the apparatus optimizing the at least one of yield or selectivity resulting in the at least one product having a calorific value of at least 12 MJ/kg.

22. The apparatus according to claim 21, wherein the resulting at least one product has a calorific value of at least 20 MJ/kg.

23. The apparatus according to claim 21, wherein the resulting at least one product has a calorific value of at least 30 MJ/kg.

24. The apparatus according to claim 21, wherein the apparatus is operated as a two-stroke machine or a four-stroke machine or a four+2*x machine, and in four+2*x operation, a third cycle or stroke of said four-stroke machine is followed by a number x of compression and expansion cycles or strokes before the at least one product is pushed out of said reactor chamber, and x is an element of natural numbers.

* * * * *